(12) United States Patent
Kandori et al.

(10) Patent No.: US 7,419,473 B2
(45) Date of Patent: Sep. 2, 2008

(54) LIVING BODY INSPECTION APPARATUS

(75) Inventors: Akihiko Kandori, Tokyo (JP); Tsuyoshi Miyashita, Fuchu (JP); Kuniomi Ogata, Kokubunji (JP); Atsushi Maki, Fuchu (JP); Daisuke Suzuki, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 65 days.

(21) Appl. No.: 11/455,191

(22) Filed: Jun. 19, 2006

(65) Prior Publication Data
US 2007/0038154 A1 Feb. 15, 2007

(30) Foreign Application Priority Data
Jul. 26, 2005 (JP) ............................. 2005-216535
Nov. 24, 2005 (JP) ............................. 2005-339533

(51) Int. Cl.
*A61B 5/117* (2006.01)
*A61B 5/103* (2006.01)
(52) U.S. Cl. ...................................... 600/595
(58) Field of Classification Search ............... 600/587, 600/595; 324/207.17, 226; 702/153, 104, 702/150, 94; 340/524, 619, 686.1; 73/865.3, 73/865.4
See application file for complete search history.

(56) References Cited

U.S. PATENT DOCUMENTS 5,744,953 A * 4/1998 Hansen .................. 324/207.17
6,148,280 A * 11/2000 Kramer ....................... 702/153
2005/0065422 A1 3/2005 Kandori et al.

* cited by examiner

*Primary Examiner*—Max Hindenburg
*Assistant Examiner*—Brian Szmal
(74) *Attorney, Agent, or Firm*—Reed Smith LLP; Stanley P. Fisher, Esq.; Juan Carlos A. Marquez, Esq.

(57) ABSTRACT

A living body inspection apparatus which quantitatively evaluates timings of movements (bending and stretching) of fingers. The apparatus includes: a movement sensor including a transmitter coil for generating a magnetic field and a plurality of receiver coils for receiving the generated magnetic field from the transmitter coil; analyzing means which analyzes time-series waveform data acquired from the movement sensor; and display means which displays a result of analysis made by the analyzing means. For comparison of waveform data, the analyzing means includes distance waveform generating means for generating distance waveforms corresponding to the waveform data, and standard point generating means for generating standard points based on standard distances in the distance waveforms.

6 Claims, 17 Drawing Sheets

LIVING BODY INSPECTION APPARATUS

CLAIM OF PRIORITY

The present application claims priority from Japanese applications JP 2005-216535 filed on Jul. 26, 2005 and JP 2005-339533 filed on Nov. 24, 2005, the contents of which are hereby incorporated by reference into this application.

FIELD OF THE INVENTION

The present invention relates to an apparatus for inspecting the movement function and more particularly to an apparatus which acquires quantitative movement data at plural locations through plural movement sensors simultaneously and makes comparison and analysis.

BACKGROUND OF THE INVENTION

Cervical spondylosis is a condition that regressive change in the cervical disc and vertebral body of the cervical spine has caused cervical disc degeneration and spur formation. Basically it is irrelevant to neurologic manifestations but clinically it involves some sort of neurologic manifestation. Clinical symptoms of cervical spondylosis are manifested by hematogenous disorders caused by direct compression of spinal nerve roots and the spinal cord or vertebral artery compression.

Clinical symptoms of cervical spondylosis, which include pain, numbness, muscular weakness, and motor disorders in the neck, shoulders, arms, and fingers, are most often manifested in fingertips. Therefore, evaluation of the motor function of fingers has been widely adopted to diagnose cervical spondylosis. Conventionally, diagnosis has relied on finger motor function evaluation through eye observation of hand clenching and unclenching movements (bending and stretching all the fingers) and by reference to findings from X-ray examinations and MRI scans.

SUMMARY OF THE INVENTION

However, the above conventional diagnosis method has the following drawback: since evaluation of the motor function is not made quantitatively, it is considered that no criterion for accurate diagnoses exists, making it somewhat difficult to determine appropriate treatment.

Accordingly, an object of the present invention is to provide a living body inspection apparatus which quantitatively evaluates timings of movements (bending and stretching) of fingers.

In order to achieve the above object, the present invention provides a living body inspection apparatus which includes: a movement sensor including a transmitter coil for generating a magnetic field and a plurality of receiver coils for receiving the generated magnetic field from the transmitter coil; analyzing means which analyzes time-series waveform data acquired from the movement sensor; and display means which displays a result of analysis made by the analyzing means.

This constitution makes it possible to evaluate timings of movements (bending and stretching) of fingers quantitatively and compare the motor functions of healthy subjects and patients with cervical spondylosis adequately.

Other aspects of the invention will be apparent from the following detailed description in this specification.

According to the present invention, a living body inspection apparatus which can quantitatively evaluate timings of movements (bending and stretching) of fingers is provided.

BRIEF DESCRIPTION OF THE DRAWINGS

The invention will be more particularly described with reference to the accompanying drawings, in which:

FIG. 3A is a front view of the coil and FIG. 3B is a side view of the coil;

FIG. 12A shows differences between channels for finger closing movement and FIG. 12B shows differences between channels for finger opening movement;

DETAILED DESCRIPTION OF THE PREFERRED EMBODIMENTS

Next, preferred embodiments of the present invention will be described in detail referring to the accompanying drawings.

Figure 1:
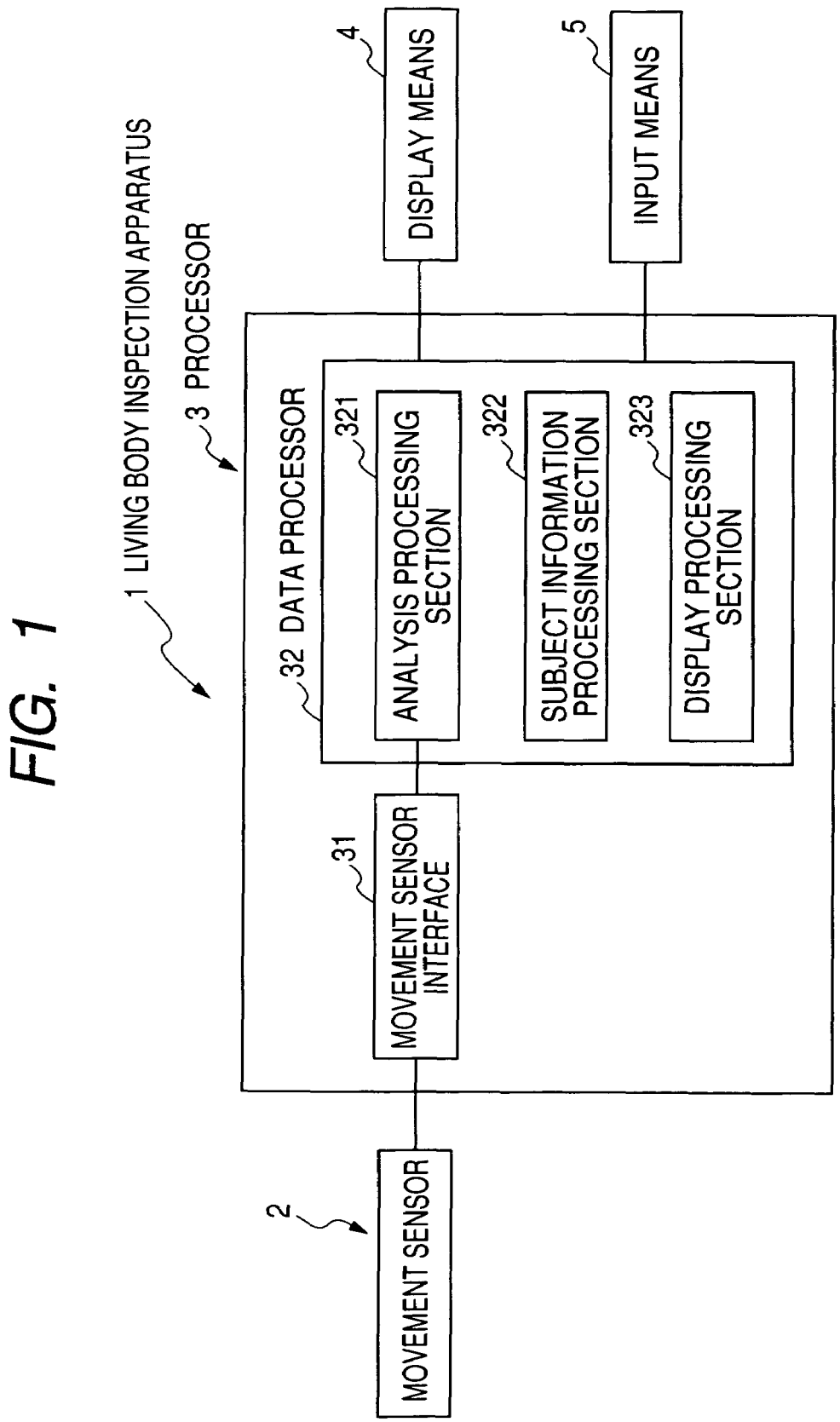
FIG. 1 is a block diagram showing the general structure of a living body inspection apparatus according to an embodiment of the invention.

FIG. 1 is a block diagram showing the general structure of a living body inspection apparatus according to an embodiment of the invention. As shown in FIG. 1, a living body inspection apparatus 1 includes a movement sensor 2, a processor 3, display means 4, and input means 5.

The movement sensor 2 detects movement of the subject in time series and acquires, as waveform data, movement information of the subject related to at least one of the following factors: distance, velocity, acceleration, and jerk.

Here, the "subject" is an object which is measured by the movement sensor 2 and anything that can move; for example, it may be a machine, animal or human being.

In this embodiment, the subject is assumed to be a patient with Parkinson's disease unless otherwise specified.

The processor 3 analyzes waveform data acquired by the movement sensor 2, extracts the feature quantity of movement, and displays the extracted feature quantity on the display means 4 as appropriate together with the subject information.

The display means 4 displays subject information and movement information which have been processed by the processor 3 and may be embodied, for example, as an LCD (Liquid Crystal Display), CRT (Cathode Ray Tube) display, or the like.

The input means 5 is intended to enable the operator (not shown) of the living body inspection apparatus 1 to enter subject information, etc. and may be embodied as a keyboard, mouse or the like. When the operator enters subject information etc., an input screen may appear on the display means 4 as a user interface which helps the operator make an entry.

Figure 2:
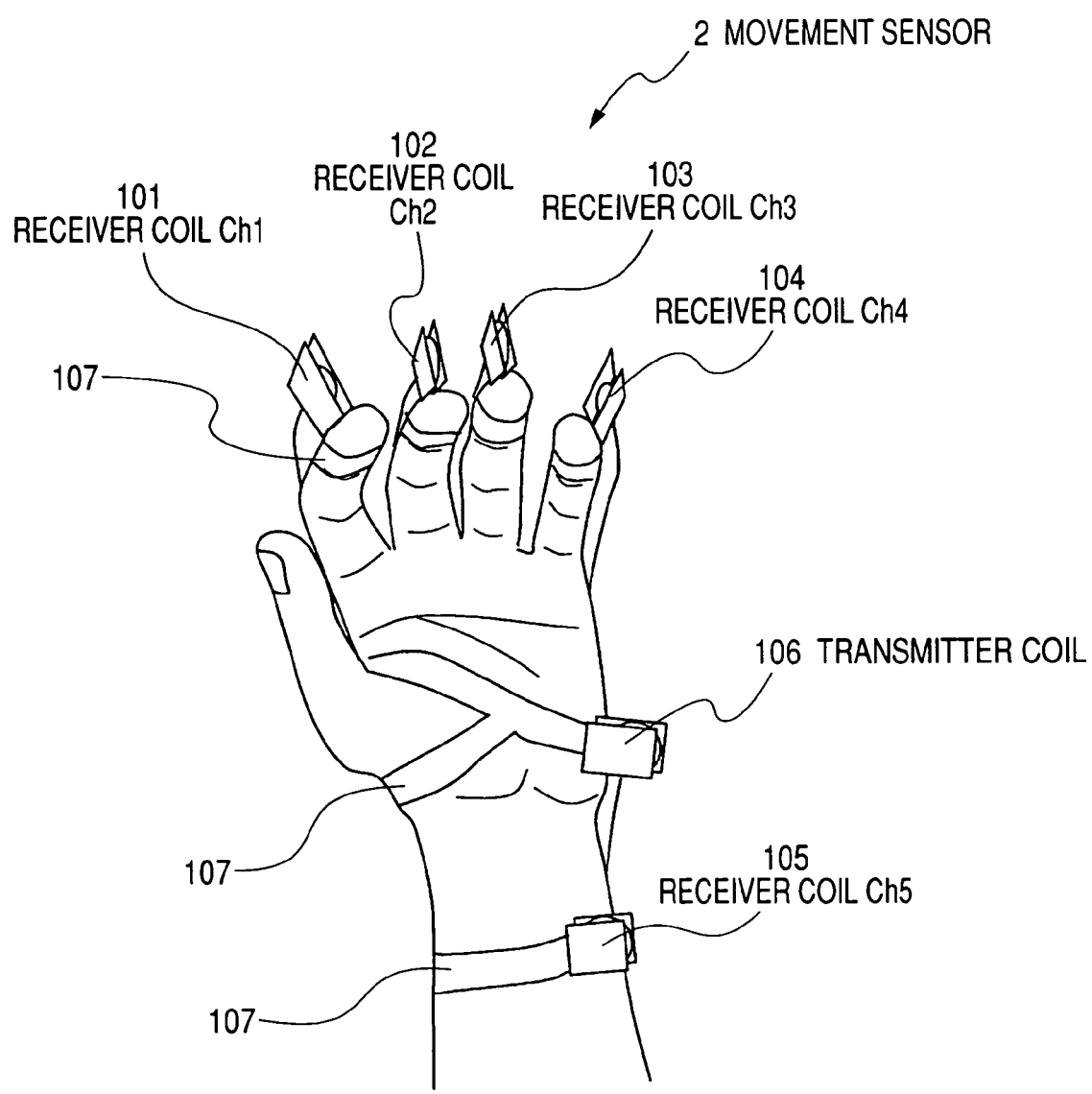
FIG. 2 is a perspective view of a movement sensor in use according to the embodiment.

FIG. 2 is a perspective view of the movement sensor in use according to this embodiment. As shown in FIG. 2, the movement sensor 2 is mainly composed of: receiver coils 101 to 104 to be attached to fingers, a receiver coil 105 to be attached to the wrist; and a transmitter coil 106 to be attached to the palm. The receiver coils 101 to 104 are attached to the forefinger, middle finger, medicinal finger and little finger, respectively.

The receiver coils 101 to 105 and the transmitter coil 106 are fixed through fixing means 107 such as Velcro (registered mark) tape in a way that the coil winding face is perpendicular to the palm surface.

Since the coils 101 to 106 are thus attached perpendicularly to the palm surface, reversal of magnetic field which is detected while the subject is bending and stretching his/her fingers is prevented.

Where to attach the receiver coils 101 to 105 and the transmitter coil 106 and the number of receiver coils in use are not limited to the abovementioned; these may vary depending on the situation as far as movement of the subject can be measured appropriately as magnetic field change.

Figure 3:
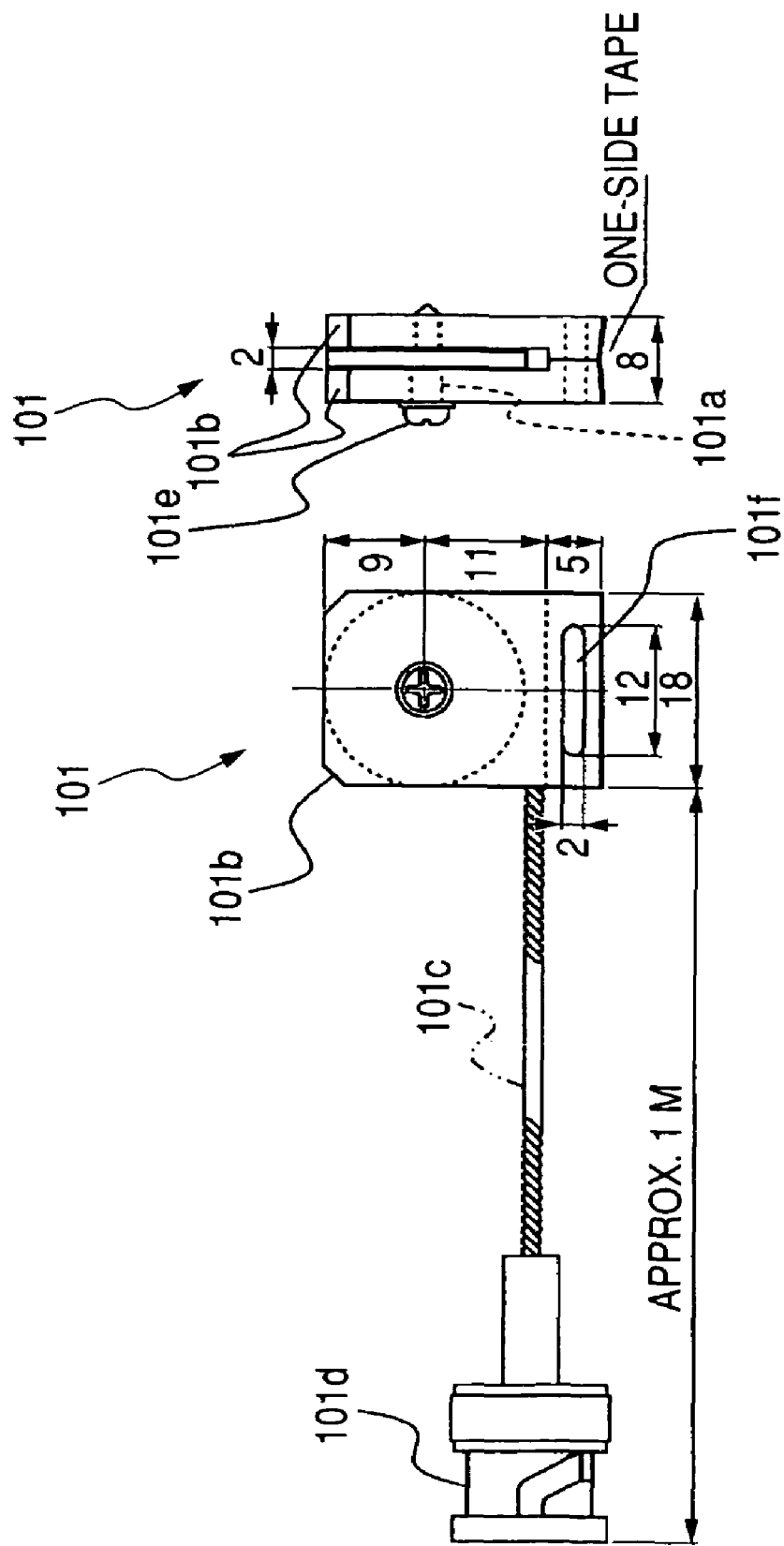
FIGS. 3A and 3B are enlarged views of a receiver coil 101 where

FIGS. 3A and 3B are enlarged views of the receiver coil 101. As shown in these figures, a coil element 101a of the receiver coil 101 is held between two flat plates made of insulating material such as plastic with its center fixed with a screw 101e. In the lower portion of the flat plates 101b, a through hole 101f is made in the thickness direction so that the fixing means 107 (FIG. 2) can be passed through it. Since the through hole 101f is made in the thickness direction of the flat plates 101b, the face of the receiver coil 101 should be perpendicular to the palm surface when the fixing means 107 is wound around a finger or the wrist and fixed.

The coil element 101a is electrically connected with the processor 3 through a conductor 101c like a twisted cable. A connector 101d which is attachable to, and detachable from, the processor 3 is provided between the conductor 101c and the processor 3. Since the coil element 101a uses a small printed circuit board, its influence on finger movement is reduced.

The dimensions indicated in FIGS. 3A and 3B are just one example of receiver coil design dimensions and may be varied depending on the measuring condition and the subject.

Figure 4:
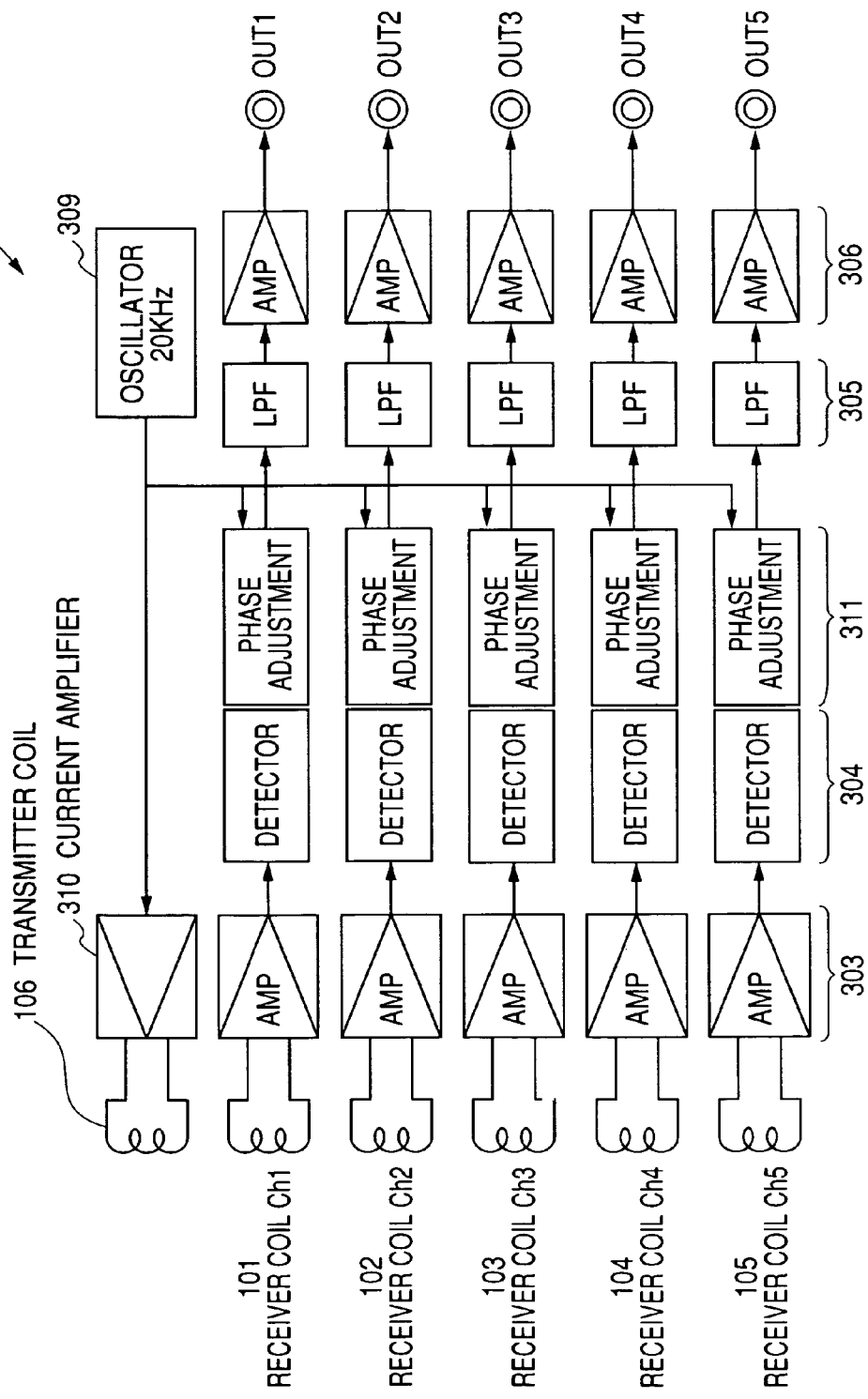
FIG. 4 is a block diagram showing one example of the structure of the movement sensor 2 according to this embodiment.

FIG. 4 is a block diagram showing one example of the structure of the movement sensor 2 according to this embodiment. As shown in FIG. 4, the five receiver coils 101 to 105 have equal circuits.

Referring to FIG. 4, an AC voltage having a specific frequency (for example, 20 kHz) is developed by an oscillator 309. The AC voltage having the specific frequency which has been developed by the oscillator 309 is converted into an AC current having a specific frequency by a current amplifier 310. The AC current which has been developed by the current amplifier 310 is allowed to flow in the transmitter coil 106. A magnetic field which has been developed by the transmitter coil 106 develops an induced electromotive force within the receiver coils 101 to 105.

The developed induced electromotive force (having the same frequency as that of the AC voltage having the specific frequency which has been developed by the oscillator 309) is amplified by a preamplifier circuit 303, and the amplified signal is sent to a detector 304.

In the detector 304, since detection is made by a signal having a specific frequency or double frequency which has been generated by the oscillator 309, an output of the oscillator 309 is adjusted in phase by a phase adjuster circuit 311 ("PHASE ADJUSTER" in the figure) before being sent to the detector 304 as a reference signal.

Also, in the case of making detection by double frequency, a frequency which is twice as high as the specific frequency, the phase adjuster circuit 328 is not always required. For a simple circuit structure that makes detection by double frequency, the specific frequency of the oscillator 309 is doubled, and after the frequency is halved by a divider, the signal is sent to the current amplifier circuit 310. The signal having a frequency twice as high as the specific frequency of the oscillator 309 is sent as the reference signal to the detector 304.

After the output of the detector 304 passes through an LPF (low-pass filter) circuit 305, it is amplified by an amplifier circuit (AMP) 306 in order to obtain a desired voltage and the amplified output 325 is sent through output terminals (OUT 1 to 5) to the processor 3 (FIG. 1). Outputs from the output terminals (OUT 1 to 5) are voltages corresponding to a relative distance D between the receiver coils 101 to 105 and the transmitter coil 106 which are attached to the subject.

In this embodiment, the subject is instructed to clench and unclench (bend and stretch) all the fingers as quickly as possible, for example, for 30 seconds.

The movement sensor 2 acquires information on these movements as waveform data corresponding to distance waveforms.

Referring back to FIG. 1, the processor 3 is further described below. The processor 3 is mainly composed of: a movement sensor interface 31 which converts the waveform data acquired by the movement sensor 2 into digital data; and a data processor 32 which mainly analyzes the digital data.

For example, the movement sensor interface 31 includes an analog-digital converter board (hereinafter called the "AD board") like one provided in a general computer and converts the waveform data of the analog signal detected by the movement sensor 2 into digital signal waveform data at a given sampling frequency and sends it to the data processor 32.

The data processor 32 includes an analysis processing section 321, a subject information processing section 322 and a display processing section 323.

The data processor 32 includes a CPU (Central Processing Unit), a memory that is made up of a ROM (read only memory) or a RAM (random access memory), and a hard disk. The constituent sections 321 to 323 of the data processor 32 are realized when a program or data stored in the memory or the hard disk is loaded in a computer (not shown). The CPU reads the program from the memory and executes arithmetic processing to perform various functions of the data processor 32.

[Analysis Processing Section]

Figure 5:
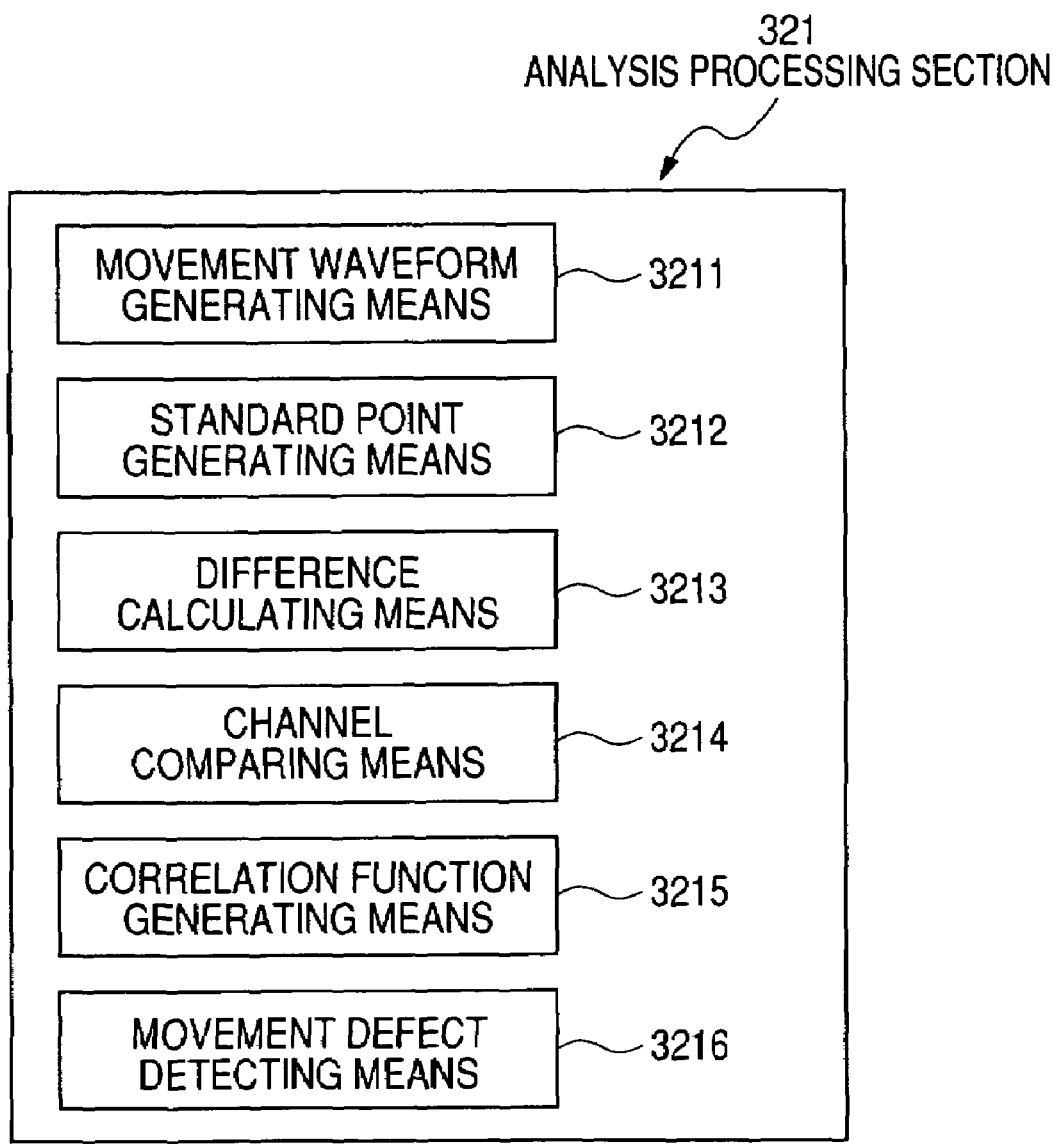
FIG. 5 is a block diagram showing the structure of an analysis processing section 321 according to this embodiment.

FIG. 5 is a block diagram showing the structure of the analysis processing section 321 according to this embodiment. The analysis processing section 321 extracts the feature quantity of movement on the basis of the waveform data sent from the movement sensor 2. Then, the result of analysis made by the analysis processing section 321 is recorded in a subject database (not shown) provided in the subject information processing section 22, read from the subject database by the display processing section 323 as appropriate, and displayed on the display means 4.

As shown in FIG. 5, the analysis processing section 321 includes movement waveform generating means 3211, standard point generating means 3212, difference calculating means 3213, channel comparing means 3214, correlation function generating means 3215, and movement defect detecting means 3216.

[Movement Waveform Generating Means]

The waveform data that has been acquired from the movement sensor 2 does not directly express a movement waveform, but expresses a voltage output corresponding to a movement waveform.

The movement waveform generating means 3211 converts the waveform data as a voltage output into a corresponding movement waveform, and time-differentiates or time-integrates the converted movement waveform to generate a distance waveform, a velocity waveform, an acceleration waveform, and a jerk waveform in a complementary manner.

A "movement waveform" includes at least one of the following types of waveform unless otherwise specified: distance waveform, velocity waveform, acceleration waveform, and jerk waveform.

[Standard Point Generating Means]

The standard point generating means 3212 generates standard points for comparison among movement waveforms measured at different channels.

Figure 6:
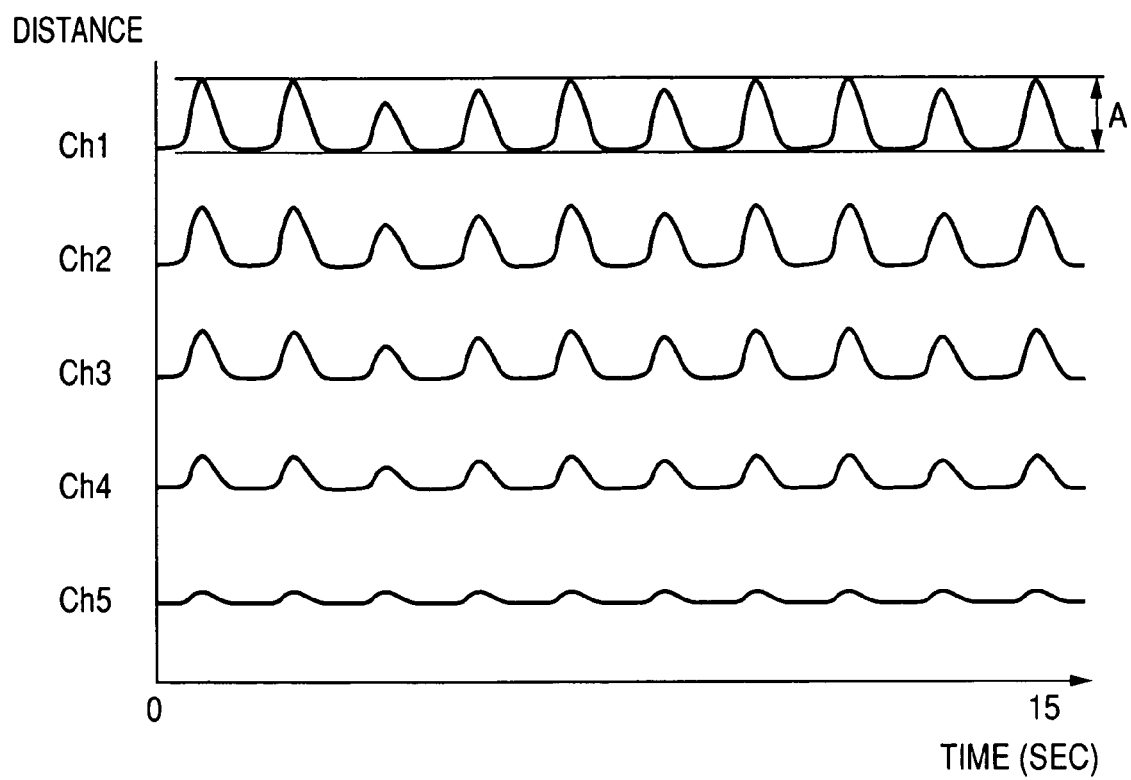
FIG. 6 shows distance waveforms obtained by measurement of finger movements of a healthy subject.
Figure 7:
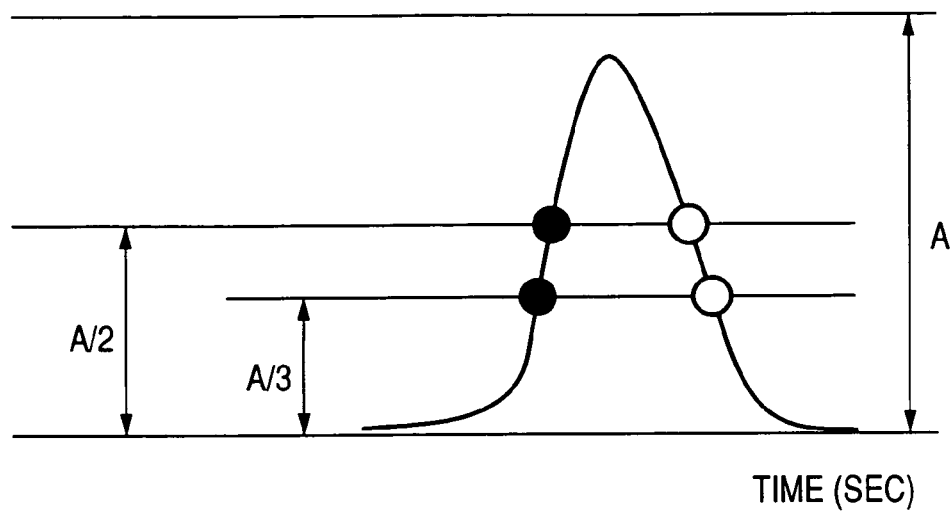
FIG. 7 illustrates how to generate standard points.

Next, the process in which the standard point generating means 3212 generates standard points in distance waveforms is explained referring to FIGS. 6 and 7.

FIG. 6 shows distance waveforms obtained by measurement of finger movements of a healthy subject.

First, the standard point generating means 3212 extracts the maximum distance A in the distance waveform at each channel as shown in FIG. 6.

Then, the standard point generating means 3212 extracts times (standard points) corresponding to half the maximum distance (A/2) or one third of the maximum distance (A/3), as shown in FIG. 7. In FIG. 7, the black circles (•) represent finger opening movement and the white circles (○) represent finger closing movement. The distance which is set to extract a standard point (half (A/2) or one third (A/3) of the maximum distance in the above case) is referred to as the "standard distance."

Figure 9:
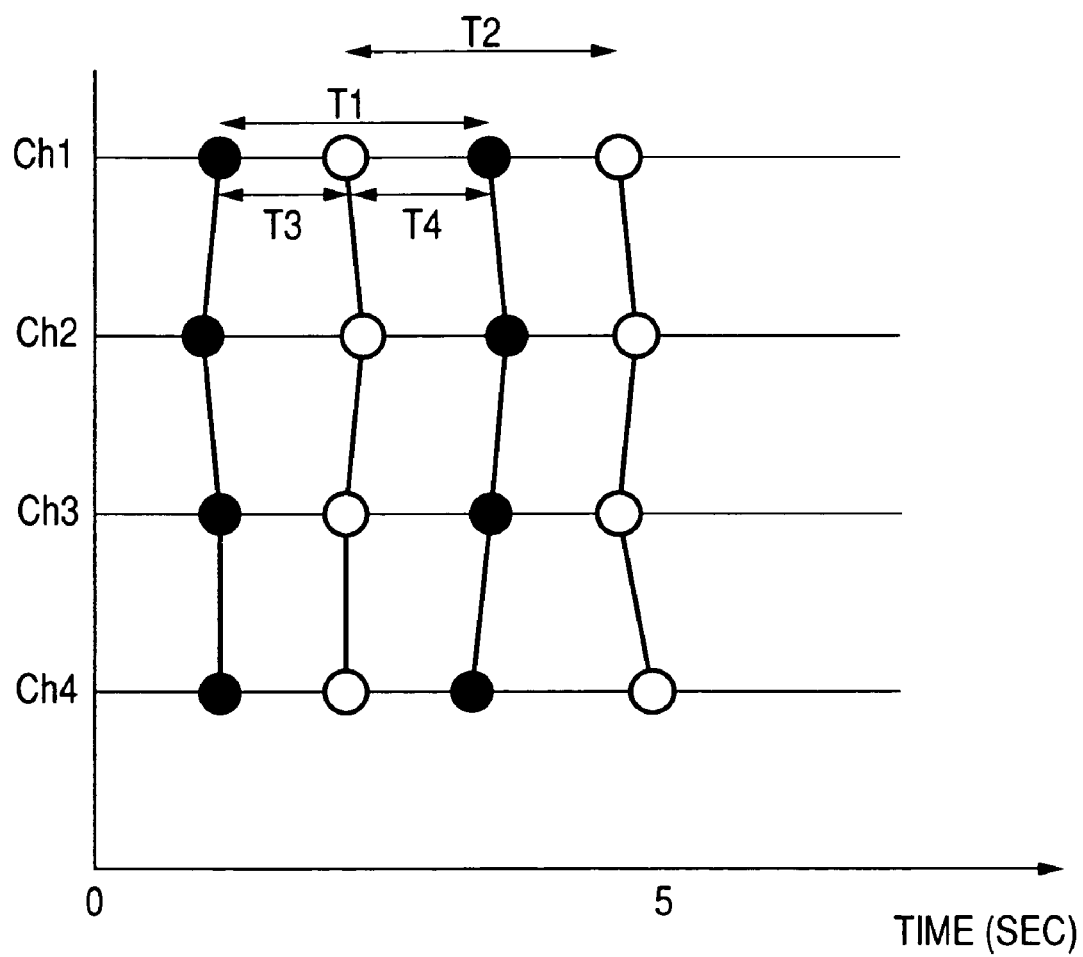
FIG. 9 is a graph obtained by plotting standard points in distance waveforms at channels.

The standard point generating means 3212 connects standard points extracted at different channels which correspond to a series of movements. The connected standard points are graphically plotted as shown in FIG. 9, which will be explained later.

As a consequence of the above process, the operator can see a plot on the display means 4 and easily make a visual check for a deviation in the subject's finger movements.

In the case of healthy subjects, virtually no movement (change in the distance between the wrist and the palm) is observed at Channel 5 as shown in FIG. 6 and analysis of measurement data for Channel 5 is omitted in this embodiment. However, in the case of patients with cervical spondylosis, a phenomenon called "trick motion" may occur because they try to compensate for a difficulty in bending their fingers by flexing their wrist unconsciously. Therefore, since the movement quantity measured at Channel 5 for patients with cervical spondylosis is larger than that for healthy subjects, it is necessary to analyze measurement data for Channel 5 in the case of patients with cervical spondylosis.

Figure 8:
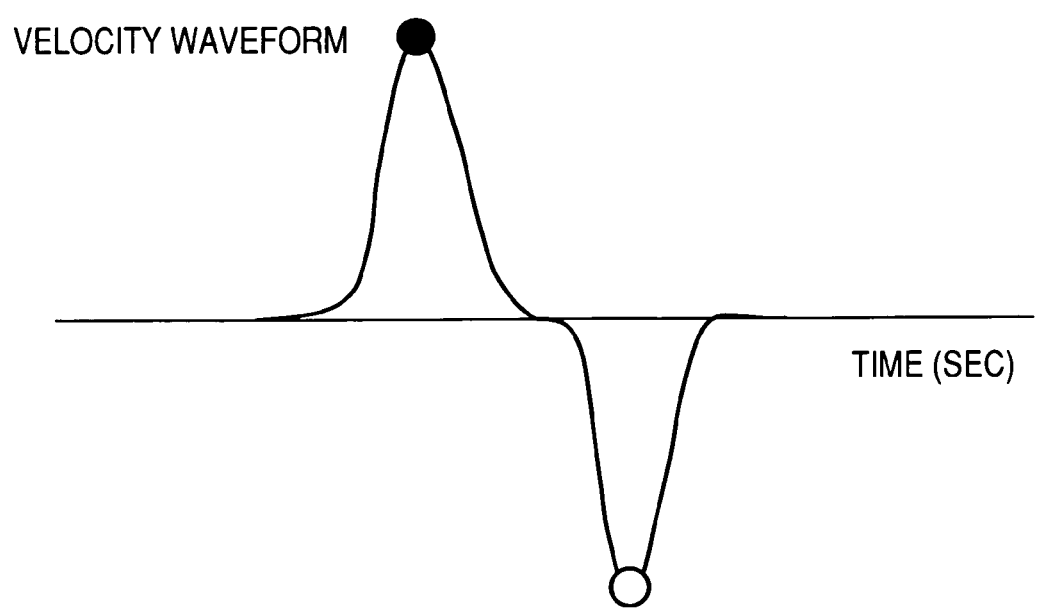
FIG. 8 illustrates how to generate standard points.

Although standard points are defined as times corresponding to half (or one third of) the maximum distance in this embodiment, standard points may be defined as times corresponding to the maximum and minimum velocities in a velocity waveform as shown in FIG. 8. In other words, as far as standard points are determined for all channels in accordance with the same rule, any approach may be used to determine standard points.

[Difference Calculating Means]

The difference calculating means 3213 extracts a movement feature by calculating time differences between standard points at a channel.

Next, the process in which the difference calculating means 3213 calculates time differences in movement waveforms is explained referring to FIG. 9. FIG. 9 is a graph obtained by plotting standard points in distance waveforms at channels.

First, as shown in FIG. 9, the difference calculating means 3213 calculates the difference (T1) from the standard point for a movement of opening a certain finger (•) to the standard point for a next movement of opening it (•).

Then the difference calculating means 3213 successively plots subsequent such standard points (•) to connect them on the basis of T1.

Similarly, as shown in FIG. 9, the difference calculating means 3213 calculates the difference (T2) from the standard point for a movement of closing a certain finger (○) to the standard point for a next movement of closing it (○).

Then the difference calculating means 3213 successively plots subsequent such standard points (○) to connect them on the basis of T2.

Figures 10A, 10B, 10C, 10D:
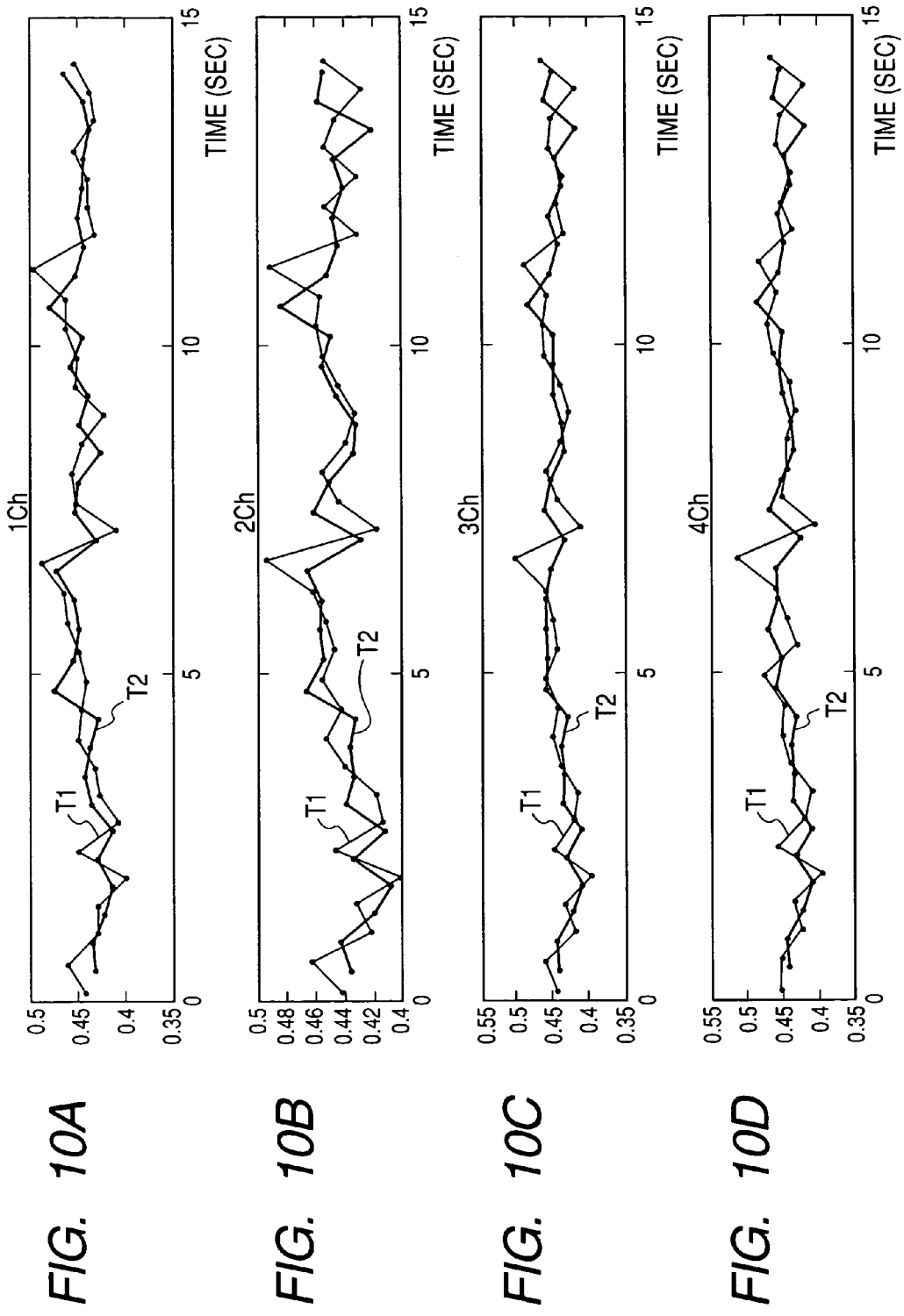
FIGS. 10A, 10B, 10C, and 10D are graphs obtained by plotting standard point differences T1 and T2, where FIG. 10A concerns Channel 1, FIG. 10B Channel 2, FIG. 10C Channel 3, and FIG. 10D Channel 4.

These connected standard points are plotted as shown in FIGS. 10A, 10B, 10C, and 10D, where FIG. 10A concerns Channel 1, FIG. 10B Channel 2, FIG. 10C Channel 3, and FIG. 10D Channel 4.

As a consequence of the above process, the operator can see these plots on the display means 4 and visually check differences between finger opening movements and finger closing movements easily.

As FIG. 9 indicates, the difference calculating means 3213 can calculate difference (T3) from the standard point for a movement of opening a certain finger (•) to the standard point for a movement of closing it (○) and connect these standard points. Conversely it can calculate difference (T4) from the standard point for a movement of closing a certain finger (○) to the standard point for a movement of opening it (•) and connect these standard points. The connected standard points are plotted as shown, for example, in FIG. 11A for Channel 1.

Figures 11A, 11B, 11C, 11D:
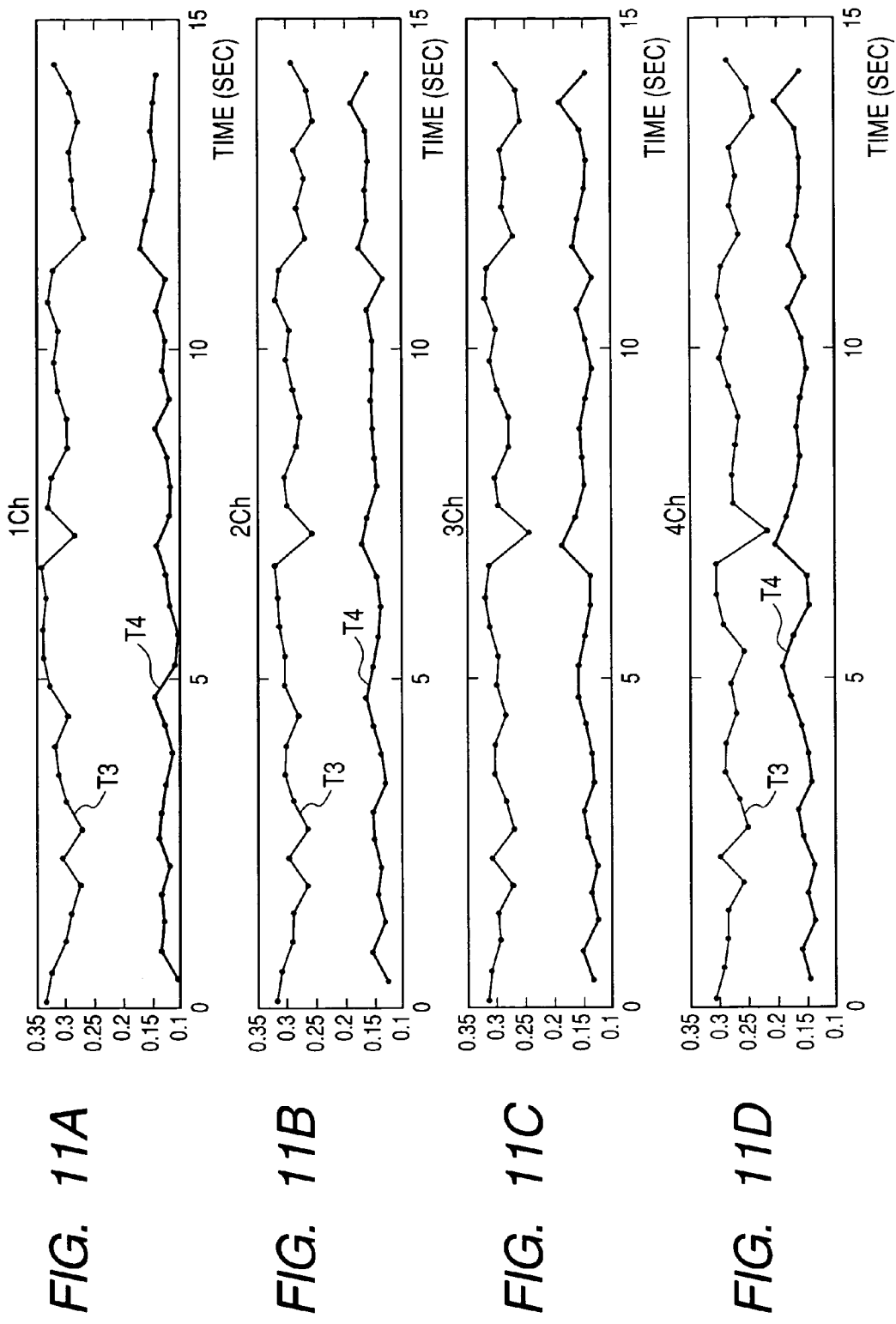
FIGS. 11A, 11B, 11C, and 11D are graphs obtained by plotting standard point differences T3 and T4, where FIG. 11A concerns Channel 1, FIG. 11B Channel 2, FIG. 11C Channel 3, and FIG. 11D Channel 4.

As FIG. 11A indicates, the plot for T3 is higher than that for T4 on average, which means that finger closing movements are quicker than finger opening movements in the case of a healthy subject. FIG. 11B concerns Channel 2, FIG. 11C Channel 3, and FIG. 11D Channel 4.

The plots for T1 and T2 which have been generated by the difference calculating means 3213 are sent to the channel comparing means 3214.

[Channel Comparing Means]

The channel comparing means 3214 calculates differences in order to make a comparison among the plots of standard points for finger closing movements (○) (or standard points for finger opening movements (•)) which are generated at different channels (see FIG. 9).

Figure 12A:
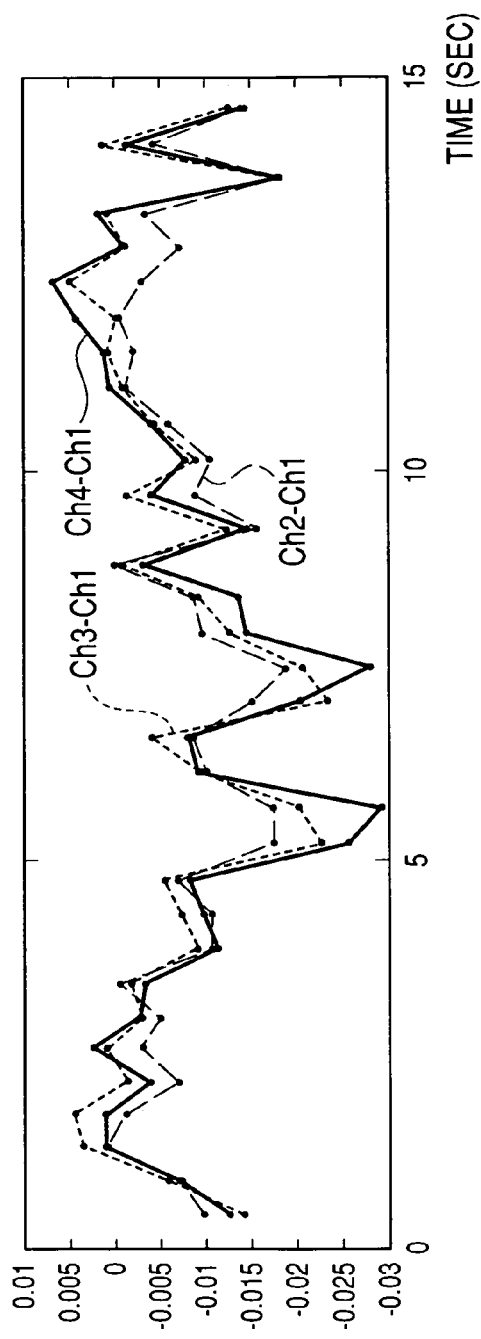
FIGS. 12A and 12B illustrate how to compare standard points for finger closing (or opening) movements between channels, where
Figure 12B:
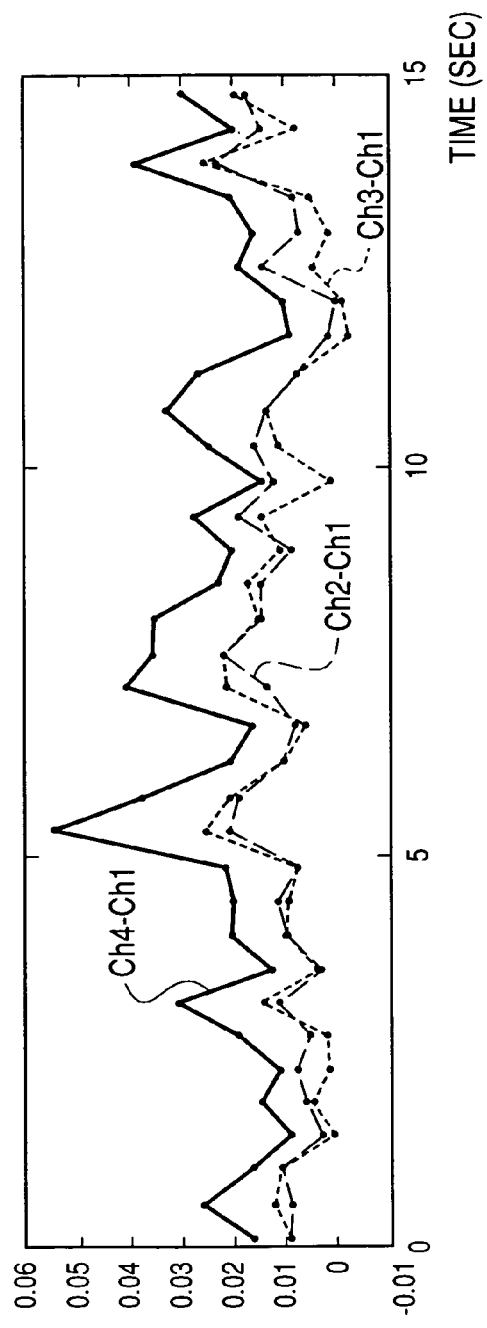

Next, the process in which the channel comparing means 3214 compares standard points (○) (or standard points (•)) among channels is explained referring to FIGS. 12A and 12B.

First, the channel comparing means 3214 decides which channel to be used as the standard channel. (In this embodiment, the standard channel is Channel 1. See Ch1 in FIG. 9).

Then, the channel comparing means 3214 calculates the difference between the standard points (○) (or standard points (•)) at the standard channel and the standard points (○) (or standard points (•)) at another channel (see Ch2 to Ch4 in FIG. 9). Specifically in this embodiment, the difference between channels refers to the difference between times T1 or T2 at different channels which are calculated by the difference calculating means 3213.

The differences between channels are plotted as shown in FIGS. 12A and 12B. FIG. 12A shows differences between channels in terms of standard points for finger closing movements (○) and FIG. 12B shows differences between channels in terms of standard points for finger opening movements (•).

As FIG. 12A indicates, the differences in standard points (○) between channels are not so different among channels; in other words, there is not so much difference at least among the finger closing movements measured at Channels 2 to 4. On the other hand, as FIG. 12B indicates, the differences in standard points (•) between channels are apparently different among channels. This means that even in the case of a healthy subject it takes longer time to open the little finger than the medicinal finger and the middle finger.

[Correlation Function Generating Means]

The correlation function generating means 3215 generates correlation functions with respect to movement waveforms measured at different channels or analyzed movement waveforms for the purpose of comparison.

Figure 13:
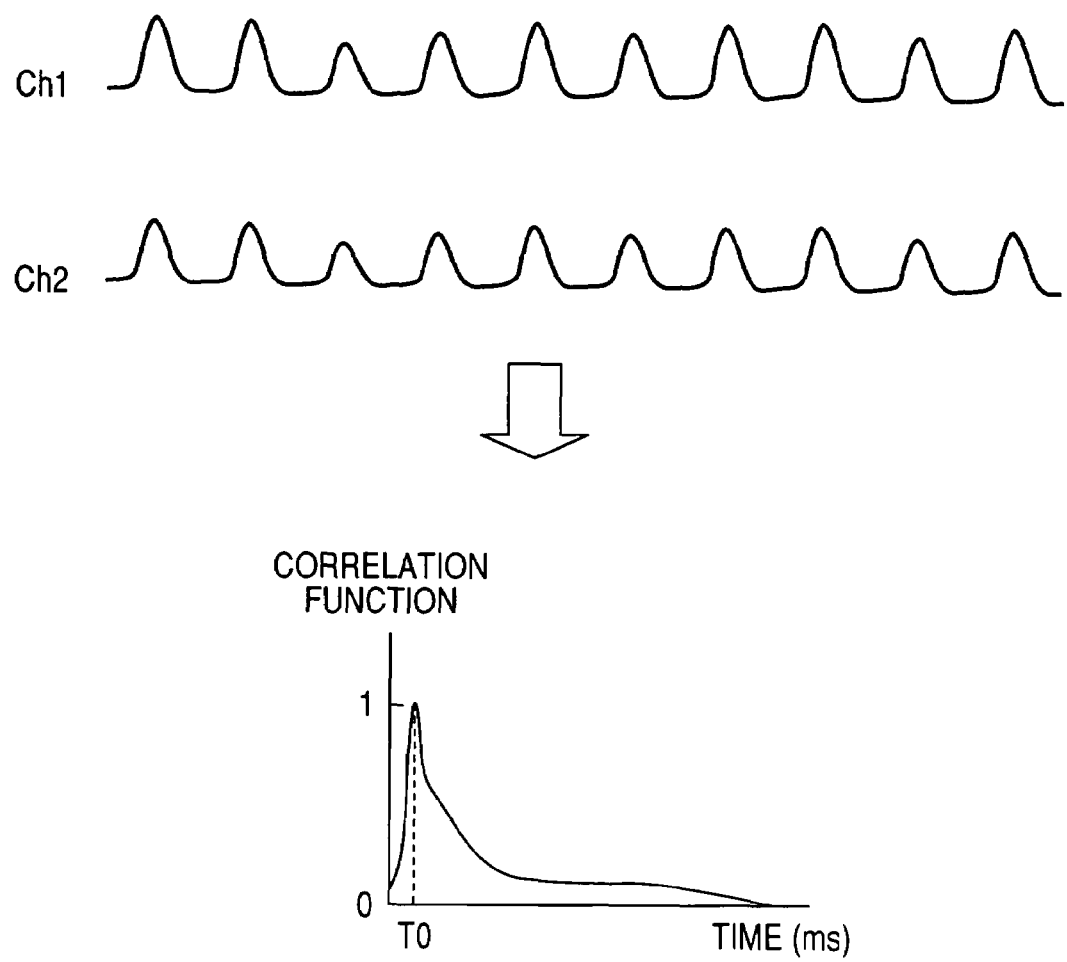
FIG. 13 schematically shows how to generate a correlation function.

As shown in FIG. 13, the correlation function generating means 3215 generates a correlation function on the basis of two movement waveforms and displays the correlation between the two movement waveforms as a function. Since the correlation between two movement waveforms is visually shown in this way, it can be easily understood.

[Movement Defect Detecting Means]

The movement defect detecting means 3216 detects whether movement of each finger of the subject is normal or not, by making use of the standard points generated by the standard point generating means 3212.

Figure 14:
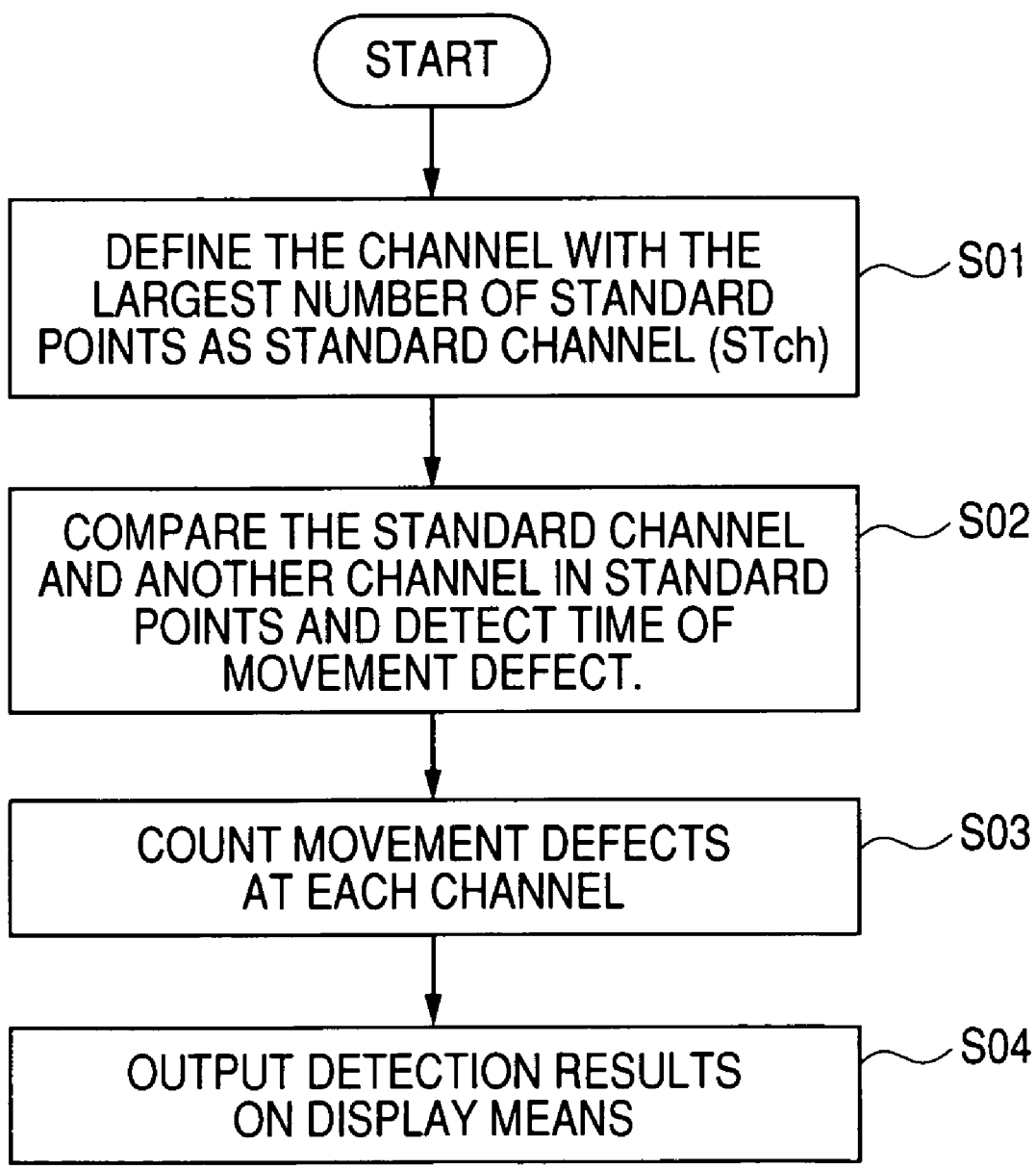
FIG. 14 is a flowchart illustrating a movement defect detecting process.
Figure 15:
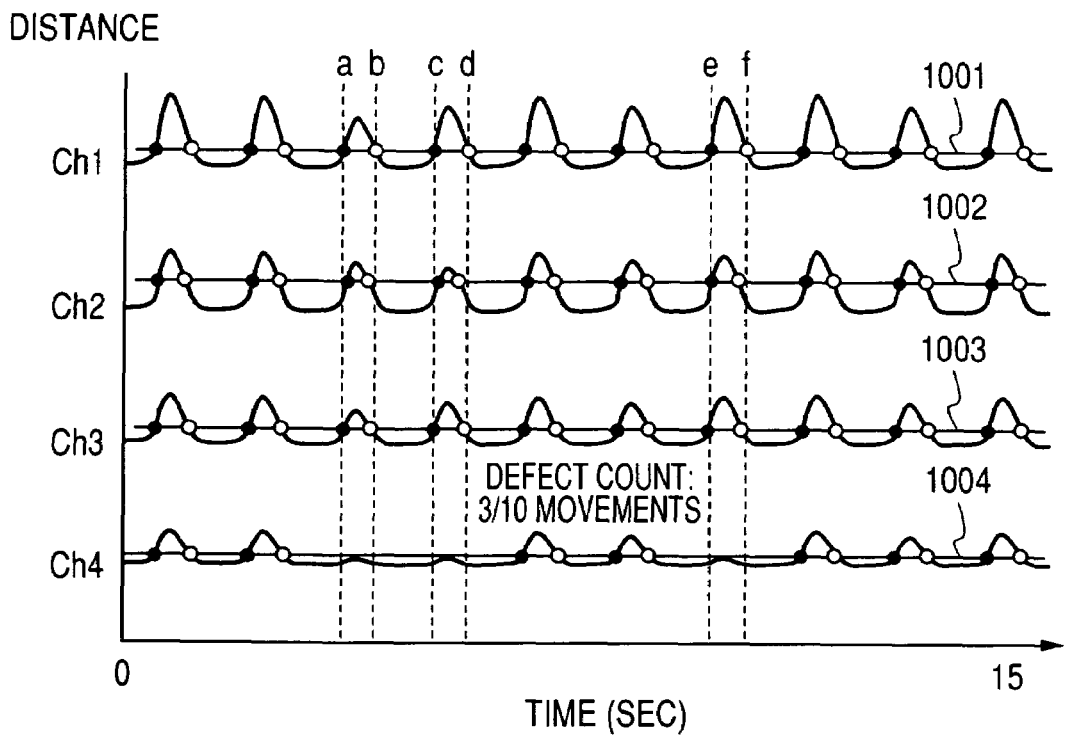
FIG. 15 illustrates how to detect a movement defect and shows distance waveforms in which standard points are generated.

Next, the movement defect detecting process which is performed by the movement defect detecting means 3216 is explained referring to FIGS. 14 and 15. FIG. 14 is a flowchart illustrating the movement defect detecting process which is performed by the movement defect detecting means 3216. FIG. 15 shows distance waveforms in which standard points have been generated.

First, the movement defect detecting means 3216 detects the channel at which the number of detected standard points is the largest and defines it as the standard channel (STch) (step S01). For example, in the case of FIG. 15, any one among Channels 1, 2, and 3 may be defined as the standard channel.

Then, the movement defect detecting means 3216 detects whether or not at another channel there is a standard point corresponding to a standard point detected at the standard channel (STch) in order to know whether the movement at that moment is defective (step S02). For example, FIG. 15 suggests that there are movement defects in time zones a-b, c-d, and e-f at Channel 4. The method which is employed at step S02 is not limited to the abovementioned method; instead, the average waveform for all channels may be used to detect movement defects.

Then, the movement defect detecting means 3216 counts movement defects detected at each channel (step S03). For example, in the case of FIG. 15, the number of movement defects for Channels 1 to 3 is zero and that for Channel 4 is 3.

Then, the movement defect detecting means 3216 outputs, on the display means 323, the number of movement defects and times of occurrence of movement defects for each channel (step S04).

[Subject Information Processing Section]

The subject information processing section 322 is provided with a subject database (not shown) which records such information as subject information and analysis results and manages information recorded in the subject database.

More specifically, in the case of conducting 1) registration, correction, deletion, retrieval, and sorting of the subject information, 2) association of the subject information with the measurement data, 3) registration, correction, and deletion of the analysis result of the measurement data (addition, correction, and deletion of items), and 4) statistical processing, the subject information processing section 322 processes main four items related to the registration, correction, and deletion of the statistical processing results in conjunction with the subject database.

Also, the subject information to be recorded in the subject database includes subject ID, name, birth date, age, body height, body weight, disorder name, and comments on the subject.

The information management as mentioned above can be readily made by the subject information processing section 322 using the conventional program and data configuration.

Also, a hard disk or the like may be used for the subject database.

[Display Processing Means]

Figure 16:
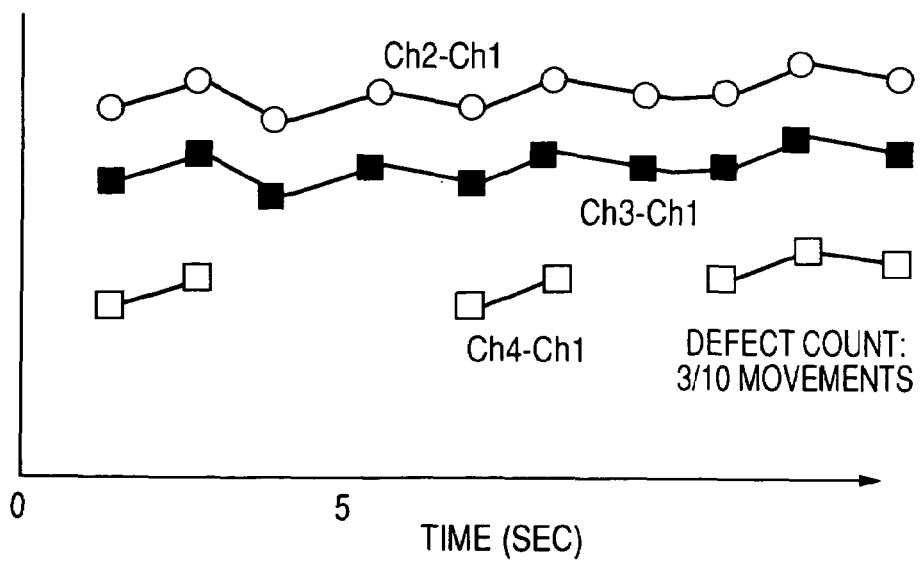
FIG. 16 is an example of display of a movement defect detection result showing differences between channels.

The display processing means 323 displays information recorded in the subject database such as subject information or analysis results on the display means 4 in a visually understandable manner, in the form of graphs or tables as appropriate. For example, the display processing means 323 not only digitally displays numerical data for the number of movement defects at each channel which have been detected by the movement defect detecting means 3216 but also can display graphs (FIGS. 12A and 12B) which the channel comparing means 3214 has produced by plotting differences between channels, without connecting differences corresponding to movement defects. As a result of display processing like this, movement defects are suggested by missing squares (□) as shown in the graph of FIG. 16 so that they can be visually identified with ease.

The display processing section 323 does not have to display all the above analysis results at the same time, and may display items that are selected by the operator as appropriate.

Since analysis results are displayed on the display means 4 in this way, it is easy to understand the motor function relating to movement of fingers or the like quantitatively and visually.

From the above discussion, it is apparent that this embodiment brings about the following effects.

Movement waveforms such as distance waveforms, velocity waveforms, acceleration waveforms, and jerk waveforms are generated and analyzed on the basis of waveform data obtained by plural receiver coils. These plural movement waveforms can be analyzed in many aspects. This living body inspection apparatus allows detailed analysis of differences in movement between patients with cervical spondylosis and healthy subjects.

The present invention is not limited to the above embodiment but it may be embodied in other various forms within the scope of its technical idea.

For instance, instead of being outputted directly as it is, the analysis result from the analysis processing section may be statistically processed before being outputted. In this case, a statistical processing section may be included in the data processor and the analysis result is divided into groups (for example, a healthy subject group and various disease groups) and statistically processed (for example, for calculation of average or variance values).

Where to attach the movement sensor 2 is not limited to the abovementioned body parts. For example, it may be attached to the fingers of both hands or a receiver coil may be attached to the thumb. Also, a receiver coil may be attached to anywhere on a finger.

Although in this embodiment voltage outputs (waveform data) measured by the movement sensor 2 are once converted into movement waveforms such as distance waveforms and standard points are then generated from the waveforms for the purpose of analysis, the present invention is not limited thereto. For example, analysis may be made directly on the basis of voltage outputs (waveform data).

A Variation of Standard Point Generating Means

A variation of standard point generating means is explained below referring to FIGS. 17 to 20. This variation of standard point generating means is different from the standard point generating means in the above embodiment in that standard points are determined based on measurement. Specifically distances measured at prescribed finger bending and stretching angles (forms) are defined as standard distances and standard points are determined based on such standard distances.

Before this variation of standard point generating means performs the standard point generation process, the living body inspection apparatus 1 should take the following steps.

Figure 17:
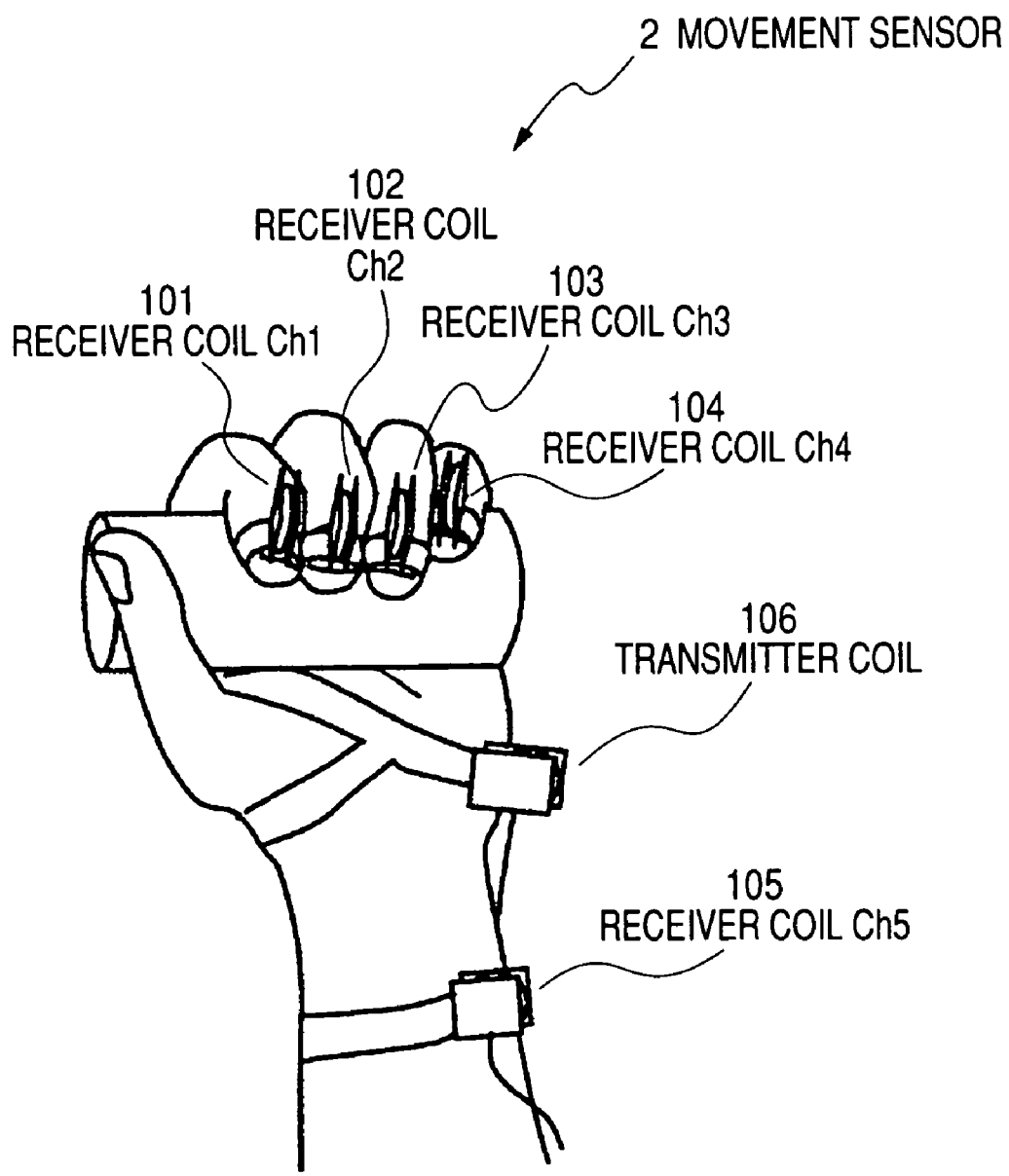
FIG. 17 shows the movement sensor arrangement for measurement of first standard distances according to a variation of the embodiment.

FIG. 17 shows the movement sensor arrangement for measurement of first standard distances. In order to measure first standard distances, the subject grasps a cylindrical bar (bar with a diameter of 30 mm or so) and voltage outputs from channels (coils 101 to 105) are acquired as shown in FIG. 17. These voltage outputs are converted into distances between the transmitter coil and the respective receiver coils, which are defined as first standard distances. In other words, the angles (forms) of fingers grasping the bar are considered to indicate that the fingers are in the course of a bending/stretching cycle and times when they pass the points of these standard distances are quantitatively analyzed.

Figure 18:
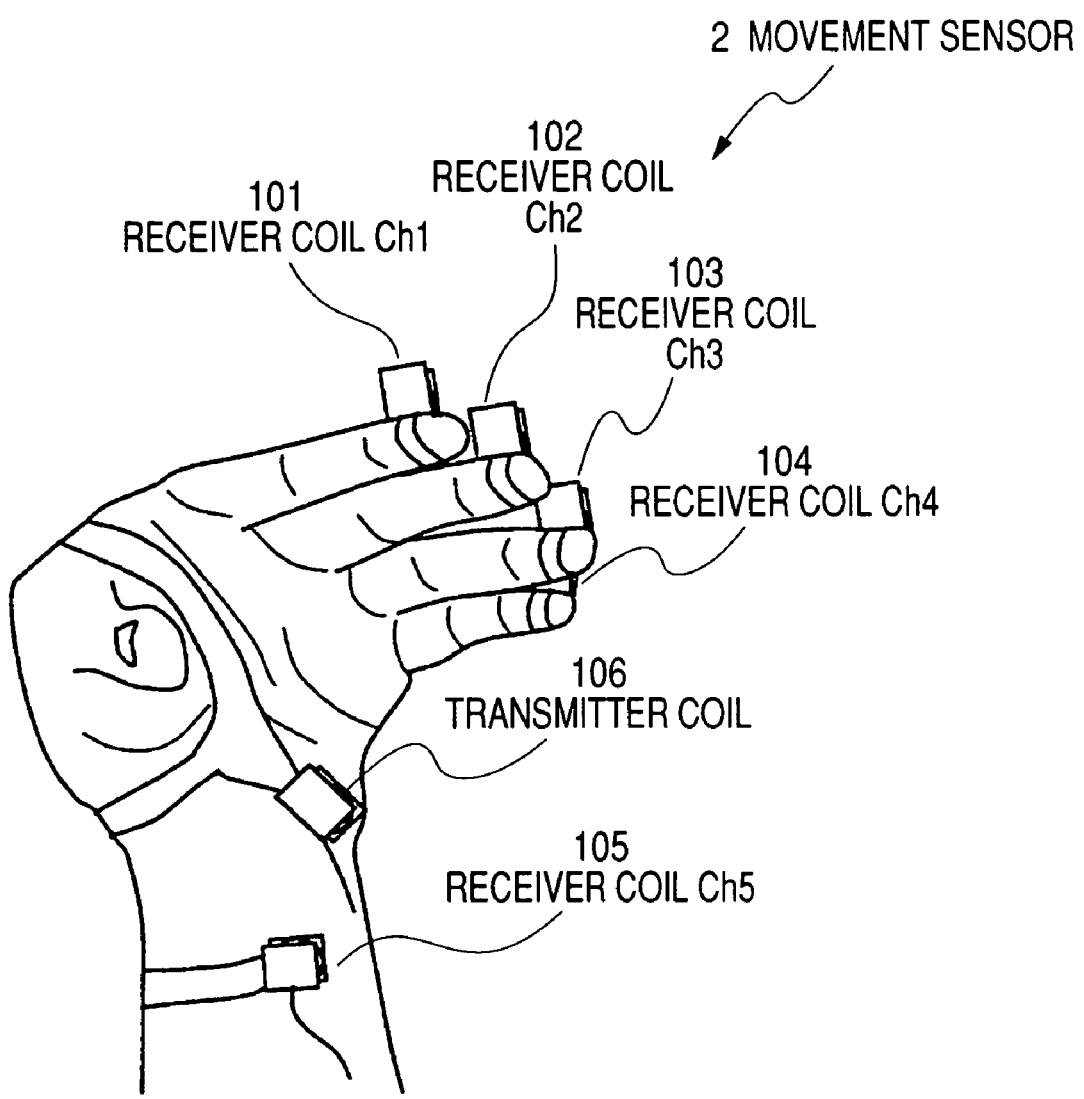
FIG. 18 shows the movement sensor arrangement for measurement of second standard distances according to the variation.

FIG. 18 shows the movement sensor arrangement for measurement of second standard distances. In order to measure second standard distances, the subject's wrist is turned approx. 90 degrees as shown in FIG. 18 and voltage outputs from the channels (coils 101 to 105) are acquired as data. These voltage outputs are converted into distances between the transmitter coil and the respective receiver coils, which are defined as second standard distances. This definition of standard distances is particularly useful to check for trick motions.

After standard distances have been thus measured in two steps, the subject is instructed to clench all his/her fingers as quickly as possible, for example, for 30 seconds. The movement sensor 2 acquires this finger movement as waveform data. The movement waveform generating means 3211 converts the waveform data into distance waveforms.

Figure 19:
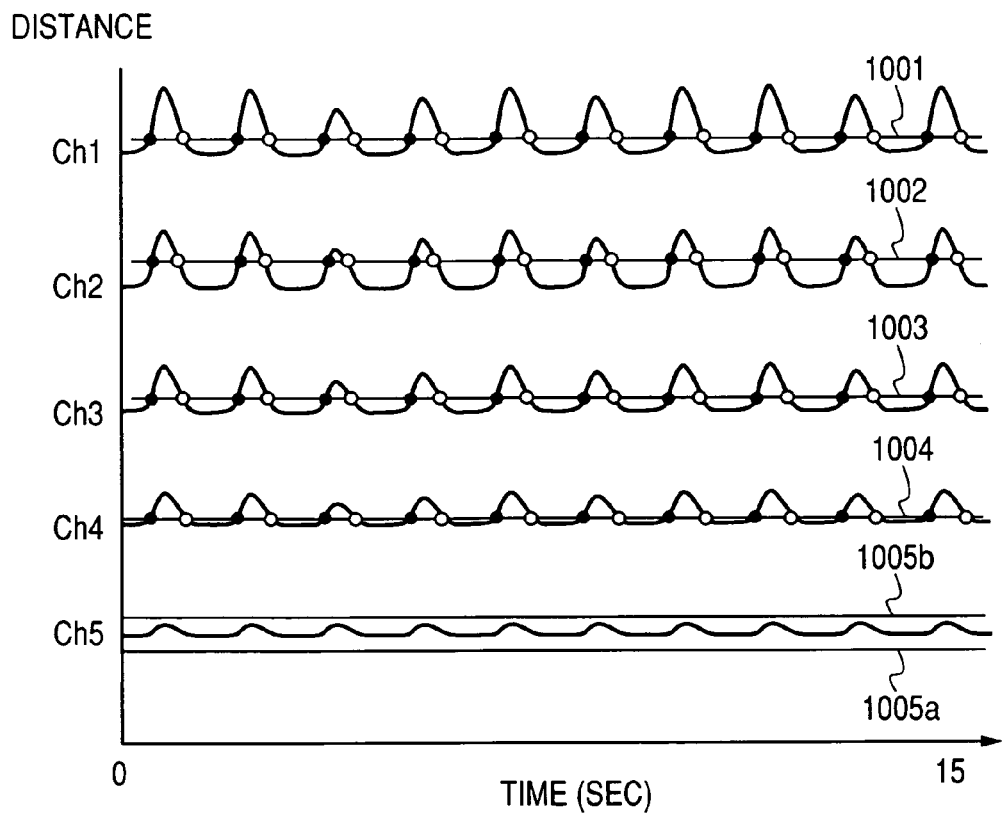
FIG. 19 is a diagram which illustrates how to generate standard points according to the variation.

Next, the process in which this variation of standard point generating means 3212 generates standard points in distance waveforms on the premise that the above steps have been taken by the living body inspection apparatus 1 is explained referring to FIG. 19.

FIG. 19 is a diagram which illustrates how to generate standard points according to the variation. As shown in FIG. 19, in order to detect finger opening and closing timings from distance waveforms on a finger-by-finger basis, the first standard distances for Channels 1 to 5 (which respectively correspond to standard lines 1001 to 1004 and 1005a in the diagram) which have been acquired by the measurement step shown in FIG. 17 (where the cylindrical bar is grasped by the fingers) are superimposed on the distance waveforms.

At the same time, the second standard distance for Channel 5 (which corresponds to standard line 1005b) which has been acquired by the measurement step shown in FIG. 18 (where the wrist is bent approx. 90 degrees) is superimposed on the distance waveform (FIG. 19).

Then, the intersections (standard points) of the distance waveform and the standard line at each channel are detected. The standard points thus obtained are used to analyze finger bending and stretching movements in the same way as described in respect to the above embodiment.

Figure 20:
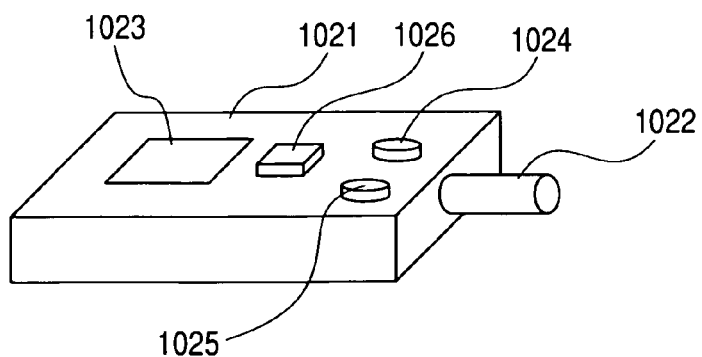
FIG. 20 is an external view of a system which easily and quickly calculates standard points and measures finger bending and stretching movements according to the variation.

FIG. 20 is an external view of a system which easily and quickly calculates standard points and measures finger bending and stretching movements according to this variation. A grip bar 1022 is fitted to a side face of an apparatus body 1021 as shown in FIG. 20. A display 1023 shows waveforms and standard points relating to finger bending and stretching movements and analysis results. Receiver coils 101 to 105 and a transmitter coil 106 are connected with the body 1021 though not shown.

Referring to FIG. 20, first a standard point calculation button 1024 is pushed to measure voltages with the subject grasping the grip bar 1022. Then a standard point calculation button 1025 is pushed to start measurement with the fingers bent as shown in FIG. 18. Finally, as the subject begins bending and stretching his/her fingers, a measurement start button 1026 is pushed to start measurement of finger movements.

What is claimed is:
1. A living body inspection apparatus comprising:
 a movement sensor for measuring movement of bending and stretching a plurality of fingers of a subject, including a transmitter coil for generating a magnetic field and a plurality of receiver coils to be attached to the plural fingers of the subject for receiving the generated magnetic field from the transmitter coil;
 analyzing means which analyzes time-series waveform data for a plurality of channels acquired from said receiver coils of the movement sensor; and display means which displays a result of analysis made by the analyzing means, wherein the analyzing means includes standard point generating means for generating standard points by detecting times in which said waveform data and a preliminary measured standard value for each corresponding channel are overlapped, difference calculating means for calculating time differences between standard points of each of said plurality of channels, and channel comparing means for calculating differences in the standard points between said plurality of channels.

2. The living body inspection apparatus as described in claim 1, wherein the standard value is a measured value from each channel with the subject grasping a bar.

3. The living body inspection apparatus as described in claim 1, wherein the standard value is a measured value from each channel with the wrist of the subject bent perpendicularly.

4. The living body inspection apparatus according to claim 1, wherein said analyzing means further comprises movement defect detecting means for detect a finger movement defect by comparing said channels in said time differences between standard points and/or calculated differences in the standard points between channels.

5. The living body inspection apparatus according to claim 1, wherein said time differences in the standard points are at least one of between times of bending, between times of stretching, and between times of bending and stretching.

6. The living body inspection apparatus according to claim 1, wherein said differences in the standard points between channels are calculated based on difference between a selected channel and other channels.

* * * * *